United States Patent [19]

Dürr

[11] Patent Number: 4,694,105
[45] Date of Patent: Sep. 15, 1987

[54] HERBICIDAL ALKOXYAMINO- AND POLYALKOXYAMINODIPHENYL ETHERS

[75] Inventor: Dieter Dürr, Bottmingen, Switzerland

[73] Assignee: Ciba-Geigy Corporation, Ardsley, N.Y.

[21] Appl. No.: 679,860

[22] Filed: Dec. 10, 1984

[30] Foreign Application Priority Data

Dec. 20, 1983 [CH] Switzerland ............ 6758/83

[51] Int. Cl.$^4$ .................. C07C 93/14; C07C 149/42
[52] U.S. Cl. .................................. 564/430; 71/121; 71/124
[58] Field of Search .............. 564/430; 71/121, 124

[56] References Cited

U.S. PATENT DOCUMENTS 4,046,798  9/1977  Bayer et al. ............ 260/465 D
4,277,624  7/1981  Yoshimoto et al. .......... 568/44
4,364,875 12/1982  Sehring et al. ............ 564/430

FOREIGN PATENT DOCUMENTS 27555  5/1981  European Pat. Off. .......... 564/430

OTHER PUBLICATIONS

Chemical Abstract-p. 283-vol. 80 (1974)-3253x.
Chemical Abstract-p. 333-vol. 79 (1973)-115299c.
Derwent 09317C/06 (7/15/78) DT 2831-262.

Primary Examiner—Charles F. Warren
Assistant Examiner—Elizabeth A. Hanley
Attorney, Agent, or Firm—Edward McC. Roberts; Meredith C. Findlay

[57] ABSTRACT

Herbicidal and plant growth regulating 3-alkoxyamino- and 3-polyalkoxyamino-2′-chloro-4-nitro-4′-trifluoromethyldiphenyl ethers of formula I

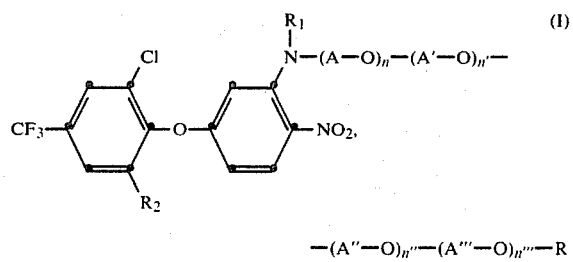

$$-(A''-O)_{n''}-(A'''-O)_{n'''}-R$$

wherein each of A, A′, A″ and A‴ is an identical or different $C_1$-$C_4$alkylene radical which may be straight chain or branched; n is a value from 1 to 5; each of n′, n″ and n‴ is zero or a value from 1 to 5; R is a $C_1$-$C_4$alkyl radical or a $C_1$-$C_4$alkylcarbonyl radical, which alkyl radicals may be substituted by halogen or cyano, or is a benzoyl or phenylsulfonyl radical which may be substituted by halogen, $C_1$-$C_4$alkyl, $C_1$-$C_4$alkoxy, $C_1$-$C_4$haloalkyl, $C_1$-$C_4$haloalkoxy or nitro, or, if A-O is not oxyethylene and/or if the sum of n+n′+n″+n‴ is greater than 1, R is also hydrogen; $R_1$ is hydrogen, $C_1$-$C_4$alkyl, $C_1$-$C_4$hydroxyalkyl, $C_2$-$C_8$alkoxyalkyl, $C_1$-$C_4$alkylcarbonyl or $C_1$-$C_4$haloalkylcarbonyl, which radicals R and $R_1$ may be branched through C-C or C-O bonds or may be linked to each other to form a ring; and $R_2$ is hydrogen, chlorine or fluorine, are suitable for selectively controlling weeds in crops of useful plants, e.g. cereals, maize, rice or soybeans.

These compounds are effective when applied at lower concentrations than the concentrations at which comparable similar known diphenyl ethers are applied. In addition, these compounds are effective against insects and representatives of the order Acarina.

10 Claims, No Drawings

HERBICIDAL ALKOXYAMINO- AND POLYALKOXYAMINODIPHENYL ETHERS

The present invention relates to novel herbicidal 3-alkoxyamino- and 3-polyalkyoxyamino-2'-chloro-4-nitro-4'-trifluoromethyldiphenyl ethers, to the preparation thereof, to compositions containing them as herbicides, and to the use thereof as selective herbicides in crops of useful plants. These compounds are also effective against insects and representatives of the order Acarina.

The novel 3-alkoxyamino- and 3-polyalkoxyamino-2'-chloro-4-nitro-4'-trifluoromethyldiphenyl ethers have the formula I

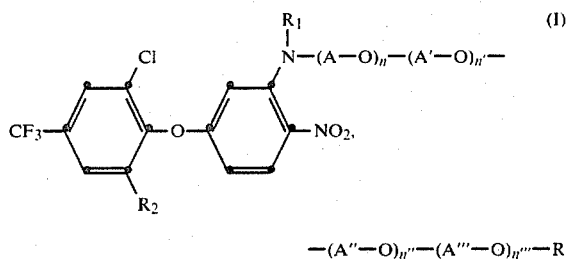

wherein each of A, A', A" and A'" is an identical or different $C_1$–$C_4$alkylene radical which may be straight chain or branched; n is a value from 1 to 5; each of n', n" and n'" is zero or a value from 1 to 5; R is a $C_1$–$C_4$alkyl radical or a $C_1$–$C_4$alkylcarbonyl radical, which alkyl radicals may be substituted by halogen or cyano, or is a benzoyl or phenylsulfonyl radical which may be substituted by halogen, $C_1$–$C_4$alkyl, $C_1$–$C_4$alkoxy, $C_1$–$C_4$haloalkyl, $C_1$–$C_4$haloalkoxy or nitro, or, if A—O is not oxyethylene and/or if the sum of n+n'+n"+n'" is greater than 1, R is also hydrogen; $R_1$ is hydrogen, $C_1$–$C_4$alkyl, $C_1$–$C_4$hydroxyalkyl, $C_2$–$C_8$alkoxyalkyl, $C_1$–$C_4$alkylcarbonyl or $C_1$–$C_4$haloalkylcarbonyl; which radicals R and $R_1$ may be branched through C—C or C—O bonds or may be linked to each other to form a ring; and $R_2$ is hydrogen, chlorine or fluorine.

In this formula the alkylene radicals A comprise methylene, ethylene, propylene and butylene such as branched 1-methylethylene, 2-methylethylene, 1-methylpropylene, 2-methylpropylene, 3-methylpropylene and 1,2-dimethylethylene. Unbranched ethylene, propylene or methylene is preferred.

The alkyl radicals may be branched or unbranched.

Herbicidal 3-(substituted)amino-2'-chloro-4-nitro-trifluoromethyldiphenyl ethers have already been postulated or prepared, but have as yet attained no importance in actual practice, q.v. for example DE-A No. 2 311 638, U.S. Pat. No. 4,046,798, DE-OS No. 2 304 006, DE-A No. 2 831 262, EP application No. 27 555 and U.S. Pat. No. 4,277,624. Surprisingly, the aminoalkyl ethers of this invention and their acid addition salts have a useful selectivity towards cereals, rice, maize and also to crops of dicot plants, e.g. soybeans, while having good herbicidal properties. Said aminoalkyl ethers appear to be effective when applied at lower concentrations than the concentrations at which comparable similar known diphenyl ethers are applied.

Among the compounds of formula I, those compounds are particularly effective wherein the alkylene groups A, A', A" or A'" are ethylene, 1-methylethylene and n-propylene. Examples of such compounds are:

3-ethoxy-diethylene glycolamino-2'-chloro-4-nitro-4'-trifluoromethyldiphenyl ether,
3-n-butoxyethylamino-2'-chloro-4-nitro-4'-trifluoromethyldiphenyl ether,
2'-chloro-3-methoxy-triethylene glycolamino-4-nitro-4'-trifluoromethyldiphenyl ether,
2'-chloro-4-nitro-3-triethylene glycolamino-4'-trifluoromethyldiphenyl ether,
2'-chloro-3-methoxy-diethylene glycol-2",3"'-propyleneamino-4-nitro-4'-trifluoromethyldiphenyl ether,
2-chloro-3-methoxy-ethylene glycol-2",3"'-propyleneamino-4-nitro-4'-trifluoromethyldiphenyl ether,
3-n-butoxy diethylene glycolamino-2'-chloro-4-nitro-4-trifluoromethyldiphenyl ether,
3-ethoxy diethylene glycol-2",3"-propyleneamino-2'-chloro-4-nitro-4'-trifluoromethyldiphenyl ether,
2'-chloro-3-methoxy-triethylene glycol-2",3"-propyleneamino-4-nitro-4'-trifluoromethyldiphenyl ether,
3-n-butoxy-diethylene glycol-tri-(2",3"-propyleneglycol)amino-2'-chloro-4-nitro-4-trifluoromethyldiphenyl ether or
2-chloro-3-(2-(2"-methoxyethyleneamino)-4-nitro-4'-trifluoromethyldiphenyl ether.

The compounds of formula I are prepared by different synthesis routes known per se.

In accordance with a first process, the 3-alkyoxyamino- and 3-polyalkoxyamino-2'-chloro-4-nitro-4'-trifluoromethyldiphenyl ethers of formula I are prepared by reacting 2'-chloro-3,4-dinitro-4'-trifluoromethyldiphenyl ethers of formula II

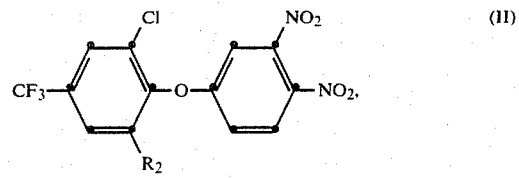

with an alkoxyamine or polyalkoxyamine of formula III

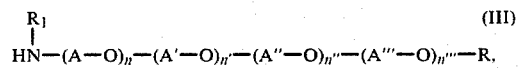

wherein A, A', A", A'", n, n', n", n'", R and $R_1$ are as defined for formula I.

The reaction is carried out advantageously in a solvent which is inert to the reactants, optionally in the presence of the molar amount of an acid acceptor. The reaction temperature can vary in the range from room temperature to the boiling point of the reaction mixture.

In accordance with a second process, the 3-alkoxyamino- and 3-polyalkoxyamino-2'-chloro-4-nitro-4'-trifluoromethyl-diphenyl ethers of formula I are also prepared by first condensing a 3-alkoxyamino- or 3-polyalkoxyaminophenyl of formula IV

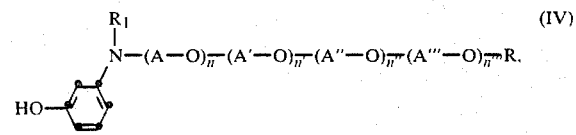

wherein A, A', A'', A''', n, n', n'', n''', R and R₁ are as defined for formula I, with a 1,2-dichloro-4-trifluoromethylbenzene of formula V

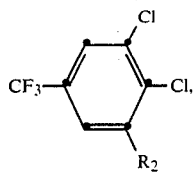

wherein R₂ is as defined for formula I, and subsequently nitrating the condensation product of formula VI

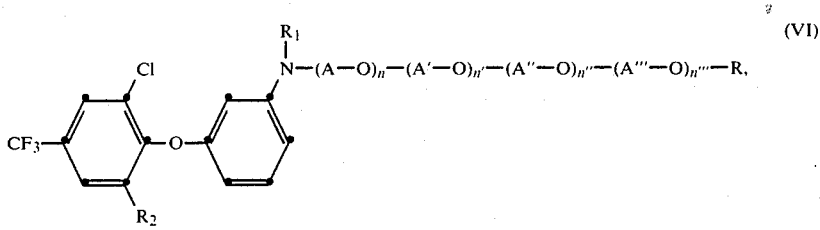

wherein A, A', A'', A''', n, n', n'', n''', R, R₁ and R₂ are as defined for formula I, with nitric acid, with the proviso that if R₁ is hydrogen, an acyl radical R₁' must first be introduced as protecting group, with acyl radical is removed after the nitration by treatment with a base.

As in the condensation of compounds of formulae II and III, the condensation of compounds of formulae IV and V is carried out in the presence of an equimolar amount of a base as acid acceptor in the temperature range from 0° C. to the boiling point of the solvent.

The nitration of the 3-alkoxyamino- or 3-polyalkoxyaminodiphenyl ether of formula VI is carried out under relatively mild conditions, under which the alkoxyamino or polyalkoxyamino radical is retained, e.g. with 1.5 to 2 times the molar amount of 100% nitric acid in glacial acetic acid. It is also possible to dissolve the 3-alkoxyamino- or 3-polyalkoxyaminodiphenyl ether of formula VI in ethylene chloride, to add cautiously at least the equimolar amount of sulfuric acid to the solution and then, with cooling at 0° to 15° C. and stirring, to add nitrating acid (conc. sulfuric acid and conc. nitric acid 1:1) slowly dropwise.

A modification of this process comprises dissolving the 3-alkoxyamino- or 3-polyalkoxyaminodiphenyl ether of formula VI in ethylene chloride and at least twice the equimolar amount of sulfuric acid and then, with cooling to 0° to 15° C. and stirring, adding potassium nitrate in portions.

It is also possible first to condense a 3,4-dichlorobenzotrifluoride of formula V with a meta-hydroxyaniline to give the 3-amino-2'-chloro-4'-trifluoromethyldiphenyl ether of formula VII

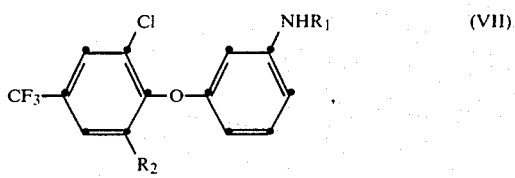

wherein R₁ is hydrogen or C₁–C₄alkyl and R₂ is as defined for formula I, and then to react this product, in an inert organic solvent and in the presence of a base, with a polyoxyalkyloxyalkyl halide of formula VIII $$X-(A-O)_n-(A'-O)_{n'}-(A''-O)_{n''}-(A'''-O)_{n'''}-R \qquad (VIII),$$

wherein X is a halogen atom, methyl sulfate or the tosylate radical and A, A', A'', A''', n, n', n'', n''' and R are as defined for formula I, and to nitrate the resultant condensation product, which is of the formula VI, with nitric acid, with the proviso that if R₁ is hydrogen, an acyl radical R₁' must first be introduced as protecting group, which acyl radical is removed after the nitration by treatment with a base.

Suitable protecting groups R₁' are the acyl radicals derived from lower fatty acids, alkylsulfonyl acids, benzenesulfonic acids, carbonic acid derivatives or benzoic acids, which radicals are introduced in the form of their halides into the secondary amino radical and are removed after the nitration by brief treatment with a base, e.g. 1 or 2N sodium hydroxide or 1 or 2N potassium hydroxide. Brief boiling in the presence of a base is generally sufficient to remove the protecting group.

Finally, compounds of formula I, wherein R is an alkyl radical, can also be prepared by reacting a 2'-chloro-4-nitro-3-hydroxyalkylamino- or 2'-chloro-4-nitro-3-polyhydroxyalkylamino-4'-trifluoromethyldiphenyl ether of formula IX

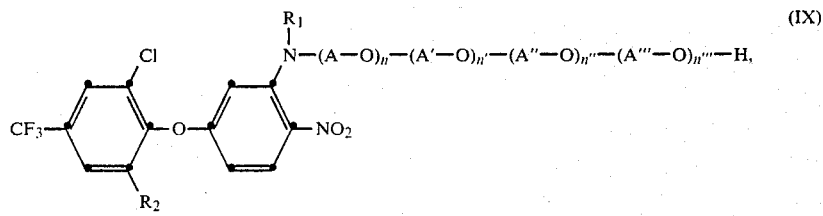

wherein A, A', A'', A''', n, n', n'', n''', R₁ and R₂ are as defined for formula I, in an inert solvent and in the presence of a base, with a reactive ester of formula X $$X-R \qquad (X),$$

wherein X is a halogen atom, a sulfonic acid or fatty acid radical.

X is preferably chlorine, bromine, the toluenesulfonic acid radical and e.g. a lower alkylsulfonic acid radical.

These reactions are preferably carried out in inert organic solvents, e.g. alkanols, higher boiling ketones or ethers, aromatic compounds, amides or sulfoxides. Examples of suitable inert organic solvents are ethanol, propanol, isopropanol, hexanol, cyclohexanol, methylethyl ketone, dioxan, tetrahydrofuran, benzene, toluene, dimethylformamide, dimethylsulfoxide and acetonitrile.

The reaction temperatures are preferably in the range from $-20°$ to $120°$ C. The reactions often exotherm readily and can be carried out at room temperature. To shorten the reaction time or to initiate the reaction, it is convenient to heat the reaction mixture briefly to boiling point.

The starting materials of formulae III and VIII are prepared by starting from the corresponding monoethers of polyalkylene glycols which are reacted, in the presence of a small amount of solvent and optionally of a catalyst, with a haogenating agent, e.g. thionyl chloride, to give the polyalkylene glycol monoether halide, viz chloride, which may be isolated from the reaction mass by distillation or immediately taken up in a solvent e.g. an alkanol or ether, and reacted with ammonia in an autoclave at more elevated temperature in the range from $50°$ to $200°$ C. and under increased pressure. The final product is dewatered by distillation with benzene or toluene and then purified by fractional distillation.

The compounds of formula I have good herbicidal properties. In high rates of application they can be used as total herbicides. However, it is more advantageous to use them in rates of application of about 0.1 to 5 kg per hectare as selective herbicides in crops of cultivated plants, either postemergence in germinating plants or preemigence in freshly sown ones. They inhibit or hinder the occurrence of dicot weeds, but especially of many monocot species such as Lolium, Alopecuris, Rottboellia, Sorghum, Digiteria, Setaria and Panicum. Cultivated plants such as cereals, barley, wheat, rye, maize or rice, and also cotton and soybeans, are wholly unharmed, or at least unharmed at a rate of application of 1 kg/ha.

The compounds of formula I can also be used for controlling ectoparasites, such as *Lucilia sericata,* and ticks in domestic animals and productive livestock, e.g. by treating animals, cowsheds, barns, stables etc., and pastures. In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera, as well as representatives of the order Acarina. The pesticidal activity of the compounds of the invention corresponds to a mortality of at least 50–60% of the pests mentioned.

Further, the compounds of formula I have advantageous growth-regulating properties (growth inhibition). The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or diocytl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils, epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich and Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of formula I, 1 to 99.9%, of a solid or liquid adjuvant, and 0 to 25%, preferably 0.1 to 25%, of a surfactant.

Preferred formulations are composed in particular of the following constituents (% = percentage by weight):
Emulsifiable concentrates
active ingredient: 1 to 20%, preferably 5 to 10%
surfactant: 5 to 30%, preferably 10 to 20%
liquid carrier: 50 to 94%, preferably 70 to 85%
Dusts
active ingredient: 0.1 to 10%, preferably 0.1 to 1%
solid carrier: 99.9 to 90%, preferably 99.9 to 99%
Suspension concentrates
active ingredient: 5 to 75%, preferably 10 to 50%
water: 94 to 25%, preferably 90 to 30%
surfactant: 1 to 40%, preferably 2 to 30%
Wettable powders
active ingredient: 0.5 to 90%, preferably 1 to 80%
surfactant: 0.5 to 20%, preferably 1 to 15%
solid carrier: 5 to 95%, preferably 15 to 90%
Granulates
active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

In the following Examples the temperatures are indicated in degrees Celsius (°C.).

EXAMPLE 1

Preparation of 3-n-butoxyoxyethylene ethylamino-2'-chloronitro-4'-trifluoromethyldiphenyl ether

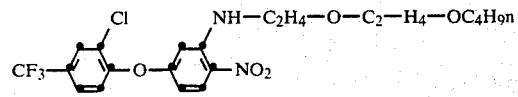

With stirring, 9 g of 2''-n-butoxy-2'-oxyethylene-2-ethylamine are added to a solution of 9 g of 2'-chloro-3,4-dinitro-4'-trifluoromethyldiphenyl ether in 30 ml of dimethylsulfoxide. The reaction mixture is stirred for 10 hours at room temperature, then poured into water and extracted with ether. The ether phase is first washed with diluted hydrochloric acid, then with water, dried over sodium sulfate and concentrated by evaporation. The residue is crystallised from a small amount of hexane, affording 7.3 g of the title compound with a melting point of 73°–74°.

The following compounds are obtained in a manner analogous to that of this Example:

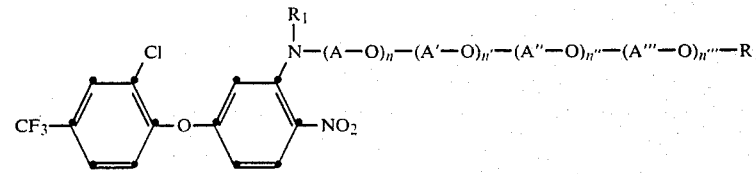

| No. | $R_1$ | $-(A-O)_n-(A'-O)_{n'}-(A''-O)_{n''}-(A'''-O)_{n'''}-R$ | Physical data |
|---|---|---|---|
| 1 | H | $C_2H_4O-CH_3$ | m.p. 86–87° |
| 2 | H | $C_2H_4O-C_2H_5$ | m.p. 79–80° |
| 3 | H | $C_2H_4O-CH(CH_3)_2$ | m.p. 69–70° |
| 4 | H | $C_2H_4O-C_4H_9n$ | m.p. 73–75° |
| 5 | H | $C_2H_4O-CH_2CH(CH_3)_2$ | |
| 6 | H | $(C_2H_4O)_2-H$ | m.p. 70–72° |
| 7 | H | $(C_2H_4O)_2-CH_3$ | m.p. 49–50° |
| 8 | H | $(C_2H_4O)_2-C_2H_5$ | m.p. 82–84° |
| 9 | H | $(C_2H_4O)_2-C_3H_7n$ | |
| 10 | H | $(C_2H_4O)_2-C_4H_9n$ | m.p. 73–74° |
| 11 | H | $(C_2H_4O)_2-CH_2CH(CH_2)_2$ | |
| 12 | H | $(C_2H_4O)_3-H$ | m.p. 67–70° |
| 13 | H | $(C_2H_4O)_4-CH_3$ | m.p. 59–60° |
| 14 | H | $(C_2H_4O)_4-C_2H_5$ | m.p. 82–84° |
| 15 | $CH_3$ | $(C_2H_4O)_3C_4H_9$ | |
| 16 | H | $C_2H_4O-C_2H_4O-C_2H_4O-CH(CH_3)_2$ | |
| 17 | H | $(C_2H_4O)_4-H$ | $n_D^{20}$ 1.5715 |
| 18 | H | $C_3H_6O-CH_3$ | m.p. 53–54° |
| 19 | H | $C_3H_6O-C_2H_5$ | m.p. 40–42° |
| 20 | H | $C_3H_6O-CH(CH_3)CH_2OH$ | |
| 21 | H | $C_3H_6O-CH(CH_3)CH_2O-C_2H_5$ | |
| 22 | H | $CH_2CH(CH_3)O-C_2H_4OH$ | |
| 23 | H | $CH_2CH(CH_3)O-C_2H_4O-CH_3$ | oil $n_D^{21}$ 1.5756 |
| 24 | H | $CH_2CH(CH_3)O-C_2H_4O-C_2H_5$ | |
| 25 | H | $CH_2CH(CH_3)O-C_2H_4O-CH(CH_3)_2$ | |
| 26 | H | $CH_2CH(CH_3)O-C_2H_4O-C_4H_9n$ | |
| 27 | H | $CH_2CH(CH_3)O-C_3H_6OH$ | |
| 28 | H | $CH_2CH(CH_3)O-C_3H_6O-CH_3$ | |
| 29 | H | $CH_2CH(CH_3)O-C_3H_6O-C_4H_9n$ | |
| 30 | H | $CH_2CH(CH_3)O-(C_2H_4O)_2CH_3$ | oil $n_D^{21}$ 1.5615 |
| 31 | H | $CH_2CH(CH_3)O-(C_2H_4O)_3CH_3$ | oil $n_D^{21}$ 1.5522 |
| 32 | H | $CH_2CH(CH_3)O-(C_2H_4O)_2C_2H_5$ | oil $n_D^{20}$ 1.5539 |
| 33 | H | $CH_2C(CH_3)_2OH$ | m.p. 78–80° |
| 34 | H | $[CH_2CH(CH_3)O]_2H$ | |
| 35 | H | $[CH_2CH(CH_3)O]_2C_2H_5$ | |
| 36 | H | $[CH_2CH(CH_3)O]_2C_4H_9n$ | |
| 37 | H | $[CH_2CH(CH_3)O]_2C_2H_4OCH_3$ | |
| 38 | H | $[CH_2CH(CH_3)O]_2C_2H_4OC_2H_5$ | |
| 39 | H | $[CH_2CH(CH_3)O]_2C_2H_4OC_4H_9n$ | |
| 40 | H | $[CH_2CH(CH_3)O]_2C_3H_6OH$ | |
| 41 | H | $[CH_2CH(CH_3)O]_2C_3H_6CH_3$ | |
| 42 | H | $[CH_2CH(CH_3)O]_3C_2H_4OH$ | |
| 43 | H | $[CH_2CH(CH_3)O]_3(C_2H_4O)_2CH_3$ | |
| 44 | H | $[CH_2CH(CH_3)O]_3(C_2H_4O)_2C_4H_9n$ | oil $n_D^{21}$ 1.4983 |
| 45 | H | $[CH_2CH(CH_3)O]_3C_3H_6OC_2H_5$ | |
| 46 | H | $(C_2H_4O)_2CH_2CH(CH_3)OCH_3$ | m.p. 48–50° |
| 47 | H | $(C_2H_4O)_2CH_2CH(CH_3)OC_2H_5$ | |
| 48 | H | $(C_2H_4O)_2CH_2CH(CH_3)OC_4H_9$ | |
| 49 | H | $(C_2H_4O)_3CH_2CH(CH_3)OH$ | |
| 50 | H | $(C_2H_4O)_3CH_2CH(CH_3)OC_2H_5$ | |
| 51 | H | $(C_2H_4O)_3CH_2CH(CH_3)OCH_2CH(CH_3)_2$ | |
| 52 | H | $(C_2H_4O)_3[CH_2CH(CH_3)O]_2CH_3$ | |
| 53 | H | $(C_2H_4O)_4H$ | m.p. 111–113° |
| 54 | H | $(C_2H_4O)_4CH_3$ | |
| 55 | H | $(C_2H_4O)_4CH(CH_3)_2$ | |
| 56 | H | $(C_2H_4O)_4C_4H_9n$ | |
| 57 | H | $(C_2H_4O)_4CH_2CH(CH_3)OH$ | |
| 58 | H | $(C_2H_4O)_4CH_2CH(CH_3)OC_2H_5$ | |
| 59 | H | $(C_2H_4O)_4[CH_2CH(CH_3)O]_2H$ | |
| 60 | H | $(C_2H_4O)_4[CH_2CH(CH_3)O]_2CH_3$ | |
| 61 | $CH_3$ | $CH(CH_3)CH_2OCH_3$ | $n_D^{21}$ 1.5672 |
| 62 | $CH_3$ | $C_2H_4OCH_3$ | $n_D^{20}$ 1.5672 |
| 63 | $CH_3$ | $CH_2CH_2OCH(CH_3)CH_2OCH_3$ | |
| 64 | $CH_3$ | $C_3H_6OH$ | m.p. 113–115° |
| 65 | $CH_3$ | $C_3H_6OC_2H_5$ | |
| 66 | $CH_3$ | $CH_2CH(CH_3)OC_2H_4OCH_3$ | |
| 67 | $CH_3$ | $CH_2CH(CH_3)O-(C_2H_4O)_2CH_3$ | |
| 68 | $CH_3$ | $CH_2CH(CH_3)O-(C_2H_4O)_3CH_3$ | |
| 69 | $CH_3$ | $CH_2CH(CH_3)O-(C_2H_4O)_3C_2H_5$ | |
| 70 | $CH_3$ | $CH_2C(CH_3)_2OH$ | |
| 71 | $CH_3$ | $(CH_2CH_2O)_3H$ | |
| 72 | $CH_3$ | $(C_2H_4O)_3CH_3$ | $n_D^{21}$ 1.5509 |
| 73 | $CH_3$ | $(CH_2CH_2O)_3C_2H_5$ | |
| 74 | H | $CH(CH_3)CH_2O(C_2H_4O)_2CH_3$ | $n_D^{21}$ 1.5615 |
| 75 | H | $CH(CH_3)CH_2O(C_2H_4O)CH_3$ | $n_D^{21}$ 1.5756 |
| 76 | H | $CH(CH_3)CH_2O(C_2H_4O)_2C_2H_5$ | $n_D^{21}$ 1.5539 |
| 77 | H | $CH(CH_3)CH_2O(C_2H_4O)_3CH_3$ | $n_D^{21}$ 1.5522 |
| 78 | H | $CH(CH_3)CH_2O(C_2H_4O)_3C_4H_9n$ | $n_D^{23}$ 1.5450 |
| 79 | H | $CH_2CH(OCH_3)_2$ | oil |
| 80 | H | $CH_2CH(OC_2H_5)_2$ | m.p. 73° |
| 81 | H | $C(CH_3)_2CH_2OH$ | m.p. 115–117° |

-continued

| No. | $R_1$ | $-(A-O)_n-(A'-O)_{n'}-(A''-O)_{n''}-(A'''-O)_{n'''}-R$ | Physical data |
|-----|-------|---------------------------------------------------------|---------------|
| 82  | H | $C(CH_3)_2CH_2OH$ | m.p. 76–79° |
| 83  | H | $C_5H_{10}O$ | oil |
| 84  | H | $CH(CH_3)CH_2OH$ | m.p. 78–79° |
| 85  | H | $[CH(CH_3)CH_2O]_2CH_3$ | $n_D^{21}$ 1.5702 |
| 86  | H | $(C_2H_4O)_2COCHCl_2$ | oil |
| 87  | H | $(C_2H_4O)_2COCH_3$ | m.p. 63–65° |
| 88  | H | $(C_2H_4O)_2COCH_2COOCH_3$ | oil |
| 89  | H | $(C_2H_4O)_2COCH_2Cl$ | oil |
| 90  | H | $(C_2H_4O)_2COCCl_3$ | oil |
| 91  | H | $CH_2CH(OH)CH_2OH$ | m.p. 118–120° |
| 92  | H | $CH_2CHOCOCH_3$ <br> $\mid$ <br> $CH_2OCOCH_3$ | m.p. 103–105° |
| 93  | H | $CH_2CH(OH)CH_2OCOCH_3$ | resin |
| 94  | H | $(C_2H_4O)_3COCH_2COCH_3$ | oil |
| 95  | H | $C_2H_4OCOCH_2CH_3$ | m.p. 67–71° |
| 96  | H | $CH_2CHOCOCH_2COCH_3$ <br> $\mid$ <br> $CH_2OCOCH_2COCH_3$ | oil |
| 97  | H | $C_2H_4OC_2H_4COCH_3$ | oil |
| 98  | H | $CH_2CH(CH_3)OCOCH_2COCH_3$ | oil |
| 99  | H | $CH_2CH(CH_3)OCH_2OC_2H_4OCH_3$ | $n_D^{23}$ 1.5620 |
| 100 | H | $CH_2OC_2H_4OCH_3$ | m.p. 62–66° |
| 101 | H | $(C_2H_4O)_3CH_2OC_2H_4OCH_3$ | $n_D^{23}$ 1.5405 |
| 102 | H | $C_2H_4OCH_2OC_2H_4OCH_3$ | m.p. 50–52° |
| 103 | H | $(C_2H_4O)_2CH_2OC_2H_4OCH_3$ | m.p. 47–48° |
| 104 | H | $C(CH_3)_2CH_2OCOCH_2Cl$ | $n_D^{20}$ 1.5786 |
| 105 | H | $C_2H_4OC_2H_4CN$ | m.p. 77–79° |
| 106 | H | $(C_2H_4O)_3C_2H_4CN$ | oil |
| 107 | H | $CH_2-CHO-CH_2$ <br> $\quad\mid\qquad\mid$ <br> $\quad CH_2-O$ | m.p. 103° |
| 108 | H | $C_2H_4O-CH-OCH(CH_3)$ <br> $\qquad\mid\qquad\mid$ <br> $\qquad CH_2\ CH_2\ CH_2$ | oil |
| 109 | H | $CH_2CHCH_2O$ <br> $\quad\mid\qquad\mid$ <br> $\quad OCH_2-CO$ | m.p. 120° Z |
| 110 | H | $CH_2CHOCO$ <br> $\quad\mid\qquad\mid$ <br> $\quad CH_2O$ | resin |
| 111 | H | $C_2H_4O-CH-O-CH_2$ <br> $\qquad\mid\qquad\mid$ <br> $\qquad CH_2\ CH_2\ CH_2$ | oil |
| 112 |   | $N-CH_2-CH-CH_2-O$ <br> $\mid\qquad\qquad\mid\qquad\quad\diagup$ <br> $CO\qquad\ O\quad\ CH_2$ <br> $\quad\diagdown\qquad\mid\qquad\diagup$ <br> $\qquad\qquad CH$ | m.p. 133° |
| 113 | H | $(C_2H_4O)_2CO$ phenyl | oil |
| 114 | $COCH_2Cl$ | $CH_2OCH_3$ | m.p. 97° |
| 115 | $COCH_2Cl$ | $CH_2OC_2H_5$ | m.p. 112–114° |
| 116 | $C_2H_4OC_3H_7i$ | $C_2H_4OC_3H_7i$ | oil |
| 117 | $C_2H_4OH$ | $(C_2H_4O)_3CH_3$ | $n_D^{21}$ 1.5356 |
| 118 | $COCH_2COCH_3$ | $CH_2CH(CH_3)OCOCH_2COCH_3$ | $n_D^{22}$ 1.5469 |
| 119 | H | $C_2H_4OSO_2$para-tolyl | m.p. 91–92° |
| 120 | H | $C_2H_4OCH-O-CH_2$ <br> $\qquad\mid\qquad\mid$ <br> $\quad CH_2\ CH_2\ CH_2$ | m.p. 62° |

EXAMPLE 2

The starting polyalkoxyamines are prepared as follows:

(a) Triethylene glycolamine $H_2N(C_2H_4O)_3H$ 168.5 g of triethylene glycol monochlorohydrine and 150 g of ammmonia in 150 ml of ethanol are stirred in an autoclave at 130° for 15 hours. After cooling, 43 g of solid sodium hydroxide are slowly added to the reaction mixture. The mixture is filtered and the solid residue is washed with alcohol. The filtrate is concentrated by evaporation, dried by azeotropic distillation with toluene and then fractionated in vacuo, affording 61 g of triethylene glycolamine which boils at 102°–106°/0.4 mbar.

(b) Diethylene glycolamine ethyl ether
$H_2N-(CH_2-CH_2-O)_2C_2H_5$ 487 ml of thionyl chloride are added dropwise to a stirred solution of 805 g of diethylene glycol monoethyl ether in 10 ml of pyridine. After all has been added, the mixture is heated to 80°. The initially vigorous evolution of gas ceases after about 3 hours. The reaction mixture is then degassed in vacuo, affording as residue 843 g of diethylene glycol monoethyl ether chloride which is taken up in 1 l of ethanol and stirred with 750 ml of ammonia in an autoclave at 130° for 15 hours. After cooling, 240 g of sodium hydroxide are cautiously added. The mixture is filtered and the residue is washed with alcohol. The filtrate is concentrated by evaporation and the residue is dried by azeotropic distillation with toluene and then purified by fractional distillation through a Vigreux column. The main fraction, diethylene glycolamine ethyl ether, distills at 73°–76°/17 mbar. Yield: 382 g (48% of theory).

The following amines are prepared in accordance with these Examples:

| | | |
|---|---|---|
| $H_2N(C_2H_4O)_2CH_3$ | b.p. 70–74°/ | mbar |
| $H_2N-CH_2CH(CH_3)O(C_2H_4O)_2CH_3$ | b.p. 78–79°/0.2 | mbar |
| $H_2N(C_2H_4O)_3CH_3$ | b.p. 74–75°/0.5 | mbar |
| $H_2N-CH_2CH(CH_3)O(C_2H_4O)CH_3$ | b.p. 98°/0.5 | mbar |
| $H_2N\ CH_2CH(CH_3)OC_2H_4OCH_3$ | b.p. 70°/12 | mbar |
| $H_2N\ CH_2CH(CH_3)O(C_2H_4O)_2C_2H_5$ | b.p. 70°/10.5 | mbar |
| $H_2N\ (C_2H_4O)_2C_4H_{9n}$ | b.p. 95–97°/13 | mbar |

The chlorides obtained by reacting the corresponding alkylene glycol with thionyl chloride in accordance with Example (b) can be isolated in pure form by distillation:

| | | |
|---|---|---|
| $Cl(C_2H_4O)_3CH_3$ | b.p. 75°/0.2 | mbar |
| $ClCH_2CH(CH_3)O\ C_2H_4OCH_3$ | b.p. 75–80°/14 | mbar |
| $ClCH_2CH(CH_3)O(C_2H_4O)_3CH_3$ | b.p. 125°/0.8 | mbar |
| $ClCH_2CH(CH_3)O(C_2H_4O)_2C_2H_5$ | b.p. 125°/12 | mbar |
| $Cl(C_2H_4O)_2C_4H_9$ | b.p. 105°/18 | mbar |

The required alkylene glycols are commercially available or can be prepared in accordance with the following Example:

(c) 1-methyl-2-(1,2-propylene glycol)diether
$CH_3O-C_2H_4OCH(CH_3)CH_2OH$

A mixture of 310.6 g of ethylene glycol monomethyl ether, 232 g of propylene oxide and 5 g of solid potassium hydroxide is stirred in an autoclave at 70° C. for one hour. After cooling, solid carbon dioxide is added to the reaction mixture. The mixture is filtered and distilled through a fractionating column. The main fraction, 1-methyl-2-(1,2-propylene glycol)ethylene glycol diether, boils at 79°–85°/12 mbar. Yield: 239 g.

The following polyoxy ethers are prepared in a manner anaogous to that of this Example:

| | | |
|---|---|---|
| $HO\ CH_2CH(CH_3)O(C_2H_4O)_2CH_3$ | b.p. 85°/0.3 | mbar |
| $HO\ CH_2CH(CH_3)O(C_2H_4O)_3CH_3$ | b.p. 140°/0.8 | mbar |
| $HO\ CH_2CH(CH_3)O(C_2H_4O)_2C_2H_5$ | b.p. 117°/12 | mbar |

EXAMPLE 3

Formulation Examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol (MG 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

EXAMPLE 4

Biological tests to determine the action of compounds of formula I

Preemergence herbicidal action

In a greenhouse, plant seeds are sown in flower pots of 12–15 cm diameter, so that per pot 10 to 25 plants can develop. Immediately after sowing, the surface of the soil is treated with an aqueous suspension of the test compounds obtained from a 10% wettable powder. Concentrations of 4 kg a.i./ha are employed. The pots are then kept in the greenhouse at 22°–25° C. and 50–70% relative humidity and the plants are watered regularly. The test is evaluated 3 weeks later. The state of the plants is assessed in accordance with the following rating:

9 = normal growth, as untreated controls
6–9 = slight damage
5 = moderate damage  2–4 = severe damage
1 = plant withered The results obtained are as follows:

| Compound No. | 8 | 12 | 13 | 23 | 30 |
|---|---|---|---|---|---|
| Plant | | | | | |
| Avena sativa | 2 | 9 | 5 | 3 | 5 |
| Setaria italica | 1 | 2 | 1 | 1 | 1 |
| Sinapis alba | 1 | 1 | 1 | 1 | 1 |
| Stellaria media | 1 | 1 | 1 | 1 | 1 |

Postemergence herbicidal action

A large number of weeds and cultivated plants, both monocots and dicots, are sprayed postemergence in the 4-to 6-leaf stage with an aqueous dispersion of test compound at a concentration of 4 kg a.i./ha, and then kept at 24°–26° C. and 45–60% relative humidity. The test is evaluated 15 days after treatment in accordance with the same rating as for the preemergence test.

The results obtained are as follows:

| Compound | 2 | | | | 18 | | | | 46 | | | | 76 | | | | 77 | | | |
|---|---|---|---|---|---|---|---|---|---|---|---|---|---|---|---|---|---|---|---|---|
| Concentration kg/ha | 1 | ½ | ¼ | ⅛ | 1 | ½ | ¼ | ⅛ | 1 | ½ | ¼ | ⅛ | 1 | ½ | ¼ | ⅛ | 1 | ½ | ¼ | ⅛ |
| Plant | | | | | | | | | | | | | | | | | | | | |
| barley | 7 | 8 | 8 | 8 | 6 | 7 | 7 | 8 | 5 | 6 | 8 | 9 | 6 | 7 | 7 | 8 | 5 | 6 | 7 | 8 |
| wheat | 7 | 8 | 8 | 8 | 5 | 6 | 7 | 8 | 5 | 8 | 9 | 9 | 7 | 8 | 8 | 8 | 5 | 6 | 7 | 8 |
| maize | 6 | 7 | 8 | 8 | 7 | 8 | 8 | 9 | 4 | 7 | 8 | 8 | 7 | 7 | 8 | 8 | 6 | 7 | 7 | 8 |
| sorghum | 4 | 6 | 7 | 8 | 5 | 6 | 7 | 8 | 6 | 8 | 9 | 9 | 7 | 7 | 8 | 8 | 7 | 7 | 8 | 8 |
| rice | 7 | 7 | 8 | 8 | 7 | 8 | 8 | 8 | 7 | 8 | 9 | 9 | 7 | 8 | 8 | 8 | 7 | 7 | 8 | 8 |
| soybean | 5 | 7 | 7 | 8 | 5 | 6 | 7 | 7 | 4 | 7 | 7 | 8 | 5 | 7 | 8 | 8 | 4 | 5 | 7 | 8 |
| Abutilon sp. | 1 | 1 | 2 | 3 | 1 | 1 | 1 | 3 | 1 | 2 | 2 | 2 | 1 | 1 | 3 | 3 | 1 | 1 | 1 | 3 |
| Amaranthus retrofl. | 1 | 1 | 1 | 1 | 1 | 1 | 1 | 1 | 1 | 1 | 1 | 1 | 1 | 1 | 2 | 3 | 1 | 1 | 1 | 1 |
| Chenopodium album | 1 | 1 | 1 | 1 | 1 | 1 | 1 | 1 | 1 | 1 | 1 | 1 | 1 | 1 | 2 | 2 | 1 | 1 | 1 | 2 |
| Solanum nigrum | 1 | 1 | 1 | 3 | 1 | 1 | 1 | 1 | 1 | 1 | 1 | 1 | 2 | 2 | 2 | 3 | 1 | 1 | 1 | 2 |
| Ipomoea | 1 | 1 | 1 | 1 | 1 | 1 | 1 | 1 | 1 | 1 | 2 | 2 | 1 | 1 | 1 | 1 | 1 | 1 | 1 | 1 |
| Sinapis alba | 2 | 2 | 2 | 2 | 1 | 1 | 2 | 3 | 1 | 1 | 1 | 1 | 1 | 1 | 2 | 2 | 1 | 1 | 1 | 1 |
| Stellaria media | 2 | 2 | 4 | 4 | 1 | 1 | 2 | 3 | 1 | 1 | 3 | 4 | 1 | 2 | 2 | 4 | 1 | 1 | 3 | 4 |
| Chrysanthemum | 1 | 1 | 1 | 1 | 1 | 1 | 1 | 1 | 1 | 1 | 2 | 2 | 1 | 1 | 1 | 2 | 1 | 1 | 1 | 2 |
| Galim aparine | 2 | 3 | 4 | 4 | 1 | 2 | 3 | 3 | 2 | 2 | 3 | 3 | 1 | 1 | 2 | 3 | 2 | 3 | 4 | 4 |
| Viola tricolor | 1 | 1 | 1 | 1 | 1 | 1 | 1 | 1 | 1 | 1 | 1 | 1 | 1 | 1 | 1 | 1 | 1 | 1 | 1 | 2 |
| Veronica | 1 | 1 | 1 | 1 | 1 | 1 | 1 | 1 | 1 | 1 | 1 | 1 | 1 | 1 | 2 | 2 | 1 | 1 | 1 | 1 |
| Beta vulgaris | 3 | 3 | 4 | 4 | 1 | 3 | 3 | 4 | 2 | 2 | 3 | 3 | 2 | 3 | 4 | 4 | 1 | 1 | 3 | 4 |

| Compound | 85 | | | | 87 | | | | 88 | | | | 89 | | | | 90 | | | |
|---|---|---|---|---|---|---|---|---|---|---|---|---|---|---|---|---|---|---|---|---|
| Concentration kg/ha | 1 | ½ | ¼ | ⅛ | 1 | ½ | ¼ | ⅛ | 1 | ½ | ¼ | ⅛ | 1 | ½ | ¼ | ⅛ | 1 | ½ | ¼ | ⅛ |
| Plant | | | | | | | | | | | | | | | | | | | | |
| barley | 5 | 7 | 7 | 8 | 7 | 8 | 9 | 9 | 8 | 8 | 9 | 9 | 2 | 8 | 8 | 8 | 8 | 8 | 8 | 9 |
| wheat | 4 | 6 | 8 | 9 | 8 | 8 | 9 | 9 | 8 | 8 | 8 | 9 | 7 | 8 | 9 | 9 | 8 | 9 | 9 | 9 |
| maize | 3 | 6 | 7 | 8 | 6 | 7 | 8 | 8 | 5 | 7 | 8 | 9 | 6 | 7 | 8 | 8 | 6 | 7 | 8 | 8 |
| sorghum | 5 | 7 | 8 | 9 | 4 | 6 | 7 | 7 | 6 | 7 | 7 | 9 | 6 | 7 | 7 | 8 | 5 | 6 | 7 | 7 |
| rice | 7 | 8 | 9 | 9 | 7 | 8 | 8 | 9 | 8 | 9 | 9 | 9 | 7 | 7 | 9 | 9 | 8 | 9 | 9 | 9 |
| soybean | 4 | 6 | 7 | 8 | 4 | 5 | 6 | 7 | 6 | 7 | 7 | 8 | 6 | 7 | 7 | 9 | 3 | 6 | 6 | 6 |
| Abutilon sp. | 1 | 2 | 2 | 3 | 1 | 1 | 2 | 2 | 1 | 1 | 2 | 2 | 1 | 1 | 1 | 1 | 1 | 1 | 1 | 1 |

-continued

| Compound | 85 | | | | 87 | | | | 88 | | | | 89 | | | | 90 | | | |
|---|---|---|---|---|---|---|---|---|---|---|---|---|---|---|---|---|---|---|---|---|
| Concentration kg/ha | 1 | ½ | ¼ | ⅛ | 1 | ½ | ¼ | ⅛ | 1 | ½ | ¼ | ⅛ | 1 | ½ | ¼ | ⅛ | 1 | ½ | ¼ | ⅛ |
| Amaranthus retrofl. | 1 | 1 | 1 | 1 | 1 | 1 | 1 | 1 | 1 | 1 | 1 | 2 | 1 | 1 | 1 | 1 | 1 | 1 | 1 | 2 |
| Chenopodium album | 1 | 2 | 2 | 3 | 1 | 1 | 1 | 2 | 1 | 1 | 1 | 2 | 1 | 1 | 1 | 1 | 1 | 1 | 2 | 2 |
| Solanum nigrum | 1 | 1 | 1 | 2 | 1 | 1 | 1 | 1 | 1 | 1 | 3 | 3 | 1 | 1 | 1 | 1 | 1 | 1 | 1 | 1 |
| Ipomoea | 1 | 1 | 1 | 1 | 1 | 1 | 3 | 3 | 2 | 2 | 2 | 3 | 1 | 1 | 2 | 3 | 1 | 1 | 2 | 2 |
| Sinapis alba | 1 | 1 | 1 | 1 | 1 | 1 | 1 | 1 | 1 | 1 | 5 | 5 | 1 | 1 | 1 | 2 | 1 | 1 | 1 | 4 |
| Stellaria media | 1 | 3 | 3 | 5 | 2 | 3 | 3 | 3 | 2 | 2 | 3 | 4 | 2 | 2 | 3 | 4 | 1 | 2 | 3 | 4 |
| Chrysanthemum | 1 | 1 | 1 | 1 | 1 | 2 | 2 | 2 | 2 | 2 | 4 | 4 | 1 | 1 | 2 | 4 | 1 | 2 | 2 | 4 |
| Galim aparine | 2 | 2 | 2 | 2 | 2 | 2 | 2 | 2 | 2 | 2 | 3 | 4 | 2 | 2 | 2 | 6 | 2 | 2 | 2 | 4 |
| Viola tricolor | 1 | 1 | 1 | 1 | 1 | 1 | 1 | 1 | 1 | 1 | 1 | 1 | 1 | 1 | 1 | 1 | 1 | 1 | 1 | 1 |
| Veronica | 1 | 1 | 1 | 1 | 1 | 1 | 1 | 2 | 1 | 1 | 1 | 2 | 1 | 1 | 1 | 1 | 1 | 1 | 1 | 1 |
| Beta vulgaris | 2 | 3 | 3 | 3 | 3 | 3 | 3 | 4 | 3 | 3 | 4 | 5 | 3 | 3 | 3 | 3 | 3 | 3 | 4 | 4 |

Selective herbicidal action on rice in postemergence application

Twenty-five-day-old rice plants are transplanted into large rectangular asbestos cement contains in a greenhouse. Seeds of the weeds occuring in rice crops, namely *Echinochloa crus galli, Cyperus difformis,* Ammania and Rotala, are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The test compound is then applied in the form an emulsifiable concentrate with a pipette between the rows of plants. The emulsifiable concentrate is diluted and applied such that it corresponds to a field application rate of 1, ½, ¼ and ⅛ kg/ha respectively. The test is evaluated 4 weeks later. The results of the test are as follows:

| Compound | 18 | | | | 46 | | | | 76 | | | | 77 | | | | 85 | | | |
|---|---|---|---|---|---|---|---|---|---|---|---|---|---|---|---|---|---|---|---|---|
| Concentration kg/ha | 1 | ½ | ¼ | ⅛ | 1 | ½ | ¼ | ⅛ | 1 | ½ | ¼ | ⅛ | 1 | ½ | ¼ | ⅛ | 1 | ½ | ¼ | ⅛ |
| Plant | | | | | | | | | | | | | | | | | | | | |
| rice | 7 | 8 | 9 | 9 | 9 | 9 | 9 | 9 | 7 | 8 | 9 | 9 | 6 | 8 | 9 | 9 | 8 | 9 | 9 | 9 |
| Echinochloa crus g. | 1 | 1 | 1 | 1 | 1 | 1 | 2 | 4 | 1 | 1 | 1 | 2 | 1 | 1 | 1 | 3 | 1 | 3 | 4 | 5 |
| Scirpus s.p. | 1 | 1 | 1 | 1 | 1 | 1 | 1 | 2 | 2 | 2 | 3 | 3 | 1 | 1 | 1 | 1 | 1 | 1 | 1 | 4 |
| Monocharia vagin. | 1 | 1 | 1 | 1 | 1 | 1 | 1 | 1 | 1 | 1 | 1 | 1 | 1 | 1 | 1 | 1 | 1 | 1 | 1 | 2 |
| Sagittaria pygmea | 2 | 2 | 3 | 3 | 3 | 3 | 4 | 4 | 3 | 4 | 4 | 4 | 1 | 2 | 3 | 5 | 3 | 3 | 4 | 4 |

Action against *Lucilia sericata* and *cuprina*

1 ml of an aqueous solution containing 0.5% of test compound is added at 50° C. to 9 ml of a culture medium. Then about 30 freshly hatched *Lucilia sericata* and *cuprina* larvae are added to the culture medium, and the insecticidal action is determined after 48 and 96 hours by evaluating the mortality rate.

In this test, compounds of formula I exhibit good activity against the Lucilia species tested.

Action against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Percentage mortality counts are made after 2 to 7 days (number of larvae unable to swim).

In this test, compounds of formula I exhibit good activity against *Aedes aegypti*.

What is claimed is:

1. A diphenyl ether of the formula

[Structure showing a diphenyl ether with Cl, CF$_3$, R$_2$ substituents on one ring, and O bridge to second ring with NO$_2$ and N(R$_1$)—(A—O)$_n$—(A'—O)$_{n'}$— group]

$$-(A''-O)_{n''}-(A'''-O)_{n'''}-R$$

wherein:
each of A, A', A" and A''' is an identical or different C$_1$–C$_4$-alkylene radical which may be straight-chain or branched;
n is a value of from 1 to 5;
each of n', n" and n''' is a value of from 0 to 5;
the sum of n+n'+n"+n''' is equal to or greater than 3;
R is hydrogen or a C$_1$–C$_4$-alkyl radical unsubstituted or substituted by halogen;
R$_1$ is hydrogen or a C$_1$–C$_4$-alkyl, C$_1$–C$_4$-hydroxyalkyl or C$_2$–C$_8$-alkoxyalkyl; and
R$_2$ is hydrogen, chlorine or fluorine.

2. A diphenyl ether of the formula

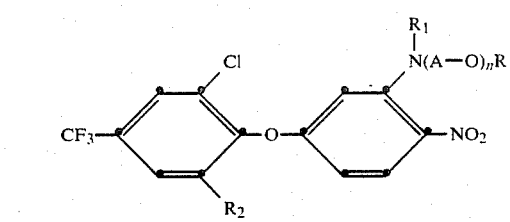

wherein:
each of A, A', A" and A''' is an identical or different C$_1$–C$_4$-alkylene radical which may be straight-chain or branched;
n is a value of from 3 to 5;

R is hydrogen or a $C_1$-$C_4$-alkyl radical unsubstituted or substituted by halogen;

$R_1$ is hydrogen, $C_1$-$C_4$-alkyl, $C_1$-$C_4$-hydroxyalkyl or $C_2$-$C_8$-alkoxyalkyl; and $R_2$ is hydrogen, chlorine or fluorine.

3. A diphenyl ether according to claim 2 wherein $(A-O)_n-R$ is $(C_2H_4O)_3-CH_3$, $R_1$ is $CH_3$ and $R_2$ is H.

4. A diphenyl ether according to claim 2 wherein $(A-O)_n-R$ is $(C_2H_4O)_3-H$ and $R_1$ and $R_2$ are H.

5. A diphenyl ether according to claim 1 wherein $(A-O)_n-(A'-O)_{n'}-(A''-O)_{n''}-(A'''-O)_{n'''}-R$ is $CH_2CH(CH_3)O-(C_2H_4O)_2-CH_3$ and $R_1$ and $R_2$ are hydrogen.

6. A diphenyl ether according to claim 1 wherein $(A-O)_n-(A'-O)_{n'}-(A''-O)_{n''}-(A'''-O)_{n'''}-R$ is $CH_2CH(CH_3)O-(C_2H_4O)_2-C_2H_5$ and $R_1$ and $R_2$ are hydrogen.

7. A diphenyl ether according to claim 1 wherein $(A-O)_n-(A'-O)_{n'}-(A''-O)_{n''}-(A'''-O)_{n'''}-R$ is $CH_2CH(CH_3)O-(C_2H_4O)_3-CH_3$ and $R_1$ and $R_2$ are hydrogen.

8. A diphenyl ether according to claim 1 wherein $(A-O)_n-(A'-O)_{n'}-(A''-O)_{n''}-(A'''-O)_{n'''}-R$ is $[CH_2CH(CH_3)O]_3-(C_2H_4O)_2$-n-$C_4H_9$ and $R_1$ and $R_2$ are hydrogen.

9. A herbicidal composition which comprises a compound of claim 1 and one or more inert adjuvants.

10. A herbicidal composition which comprises a compound of claim 2 and one or more inert adjuvants.

* * * * *